United States Patent [19]

Hama et al.

[11] Patent Number: 4,612,557

[45] Date of Patent: Sep. 16, 1986

[54] HYDROXYDIPHENYL SULFONE DERIVATIVE AND HEAT-SENSITIVE RECORDING MATERIAL USING THE DERIVATIVE

[75] Inventors: Fumio Hama, Osaka; Toshitake Suzuki, Kobe; Mitsuru Kondo, Hyogo, all of Japan

[73] Assignee: Kanzaki Paper Manufacturing Co. Ltd., Tokyo, Japan

[21] Appl. No.: 800,750

[22] Filed: Nov. 22, 1985

[30] Foreign Application Priority Data

Nov. 30, 1984 [JP] Japan .................................. 59-254758

[51] Int. Cl.$^4$ .............................................. B41M 5/18
[52] U.S. Cl. .................................... 346/216; 346/225; 427/150
[58] Field of Search ....................... 346/216, 217, 225; 427/150, 151, 152

[56] References Cited

U.S. PATENT DOCUMENTS 4,453,744  6/1984  Würmli et al. ...................... 346/216
4,536,779  8/1985  Nachbur et al. ..................... 346/216

*Primary Examiner*—Bruce H. Hess
*Attorney, Agent, or Firm*—Murray and Whisenhunt

[57] ABSTRACT

A hydroxydiphenyl sulfone derivative represented by the formula (I) is a novel compound and a heat-sensitive recording material which comprises at least one of the derivatives as a color acceptor not only has an excellent recording sensitivity, resistances to plasticizer and diazo developer but also suits to high-speed recording, has an excellent storage stability of record images and does not decrease in whiteness of the background,

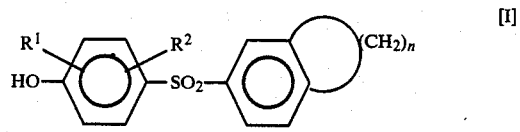

wherein $R^1$ and $R^2$ are each hydrogen, halogen, lower alkyl, lower alkoxyl or hydroxyl and n is an integer of 3 or 4.

2 Claims, No Drawings

HYDROXYDIPHENYL SULFONE DERIVATIVE AND HEAT-SENSITIVE RECORDING MATERIAL USING THE DERIVATIVE

The invention relates to a hydroxydiphenyl sulfone derivative, more particularly to a novel derivative capable of providing a heat-sensitive recording material suited to high-speed recording and having an excellent storage stability of record images without entailing a decrease in whiteness of the background, and also to a heat-sensitive recording material employing the derivative.

Heat-sensitive recording materials are well known which are adapted to produce record images by thermally contacting a colorless or pale-colored basic dye with an organic or inorganic color acceptor for a color forming reaction.

With remarkable progress in heat-sensitive recording systems in recent years, heat-sensitive facsimile systems, heat-sensitive printers, etc. are made operable at a high speed. For example, heat-sensitive facsimile systems produce a copy of A4 size within 20 seconds, and heat-sensitive printers achieve a recording speed of at least 120 characters/sec. For use with such high-speed hardware, heat-sensitive recording materials must meet the requirements of high-speed recording.

With a rapid popularization of heat-sensitive facsimile systems, heat-sensitive printers, etc., the heat-sensitive recording material has become used in a wide field. For example, it is often used in contact with a plastic film or stored in a state superposed on a diazo type copy or the like. The heat-sensitive recording material, however, fades in color easily when contacted with a plastic film and causes a color-change (fogging phenomenon) in the background when placed into contact with a diazo type copy, especially with the copy just made.

In view of the above, we have investigated to develop a heat-sensitive recording material suited to high-speed recording without entailing the above defects, and found that the fading of record images and fogging in the background are attributable to an interaction of a color acceptor and a plasticizer in the plastic film or petroleums in the diazo type copying developer.

An object of the invention is to provide a novel hydroxydiphenyl sulfone derivative which is useful as a color acceptor of a heat-sensitive recording material.

Another object of the invention is to provide a heat-sensitive recording material which has an excellent recording sensitivity and resistances to plasticizer and diazo developer.

Still another object of the invention is to provide a heat-sensitive recording material which suits to high-speed recording, has an excellent storage stability of record images and does not decrease in whiteness of the background.

The above and other objects of the invention will become apparent from the following description.

The present invention provides a hydroxydiphenyl sulfone derivative represented by the formula [I] and a heat-sensitive recording material which comprises at least one of the derivatives as a color acceptor,

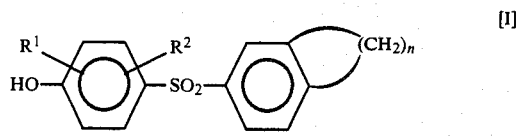

wherein $R^1$ and $R^2$ are each hydrogen, halogen, lower alkyl, lower alkoxyl or hydroxyl and n is an integer of 3 or 4.

In the formula, preferable examples of halogen atoms are chlorine, bromine and fluorine. Preferred examples of alkyl groups are methyl, ethyl, propyl, butyl and like lower alkyl groups. Examples of preferred alkoxyl groups are methoxy, ethoxy, propoxy, butoxy and like lower alkoxyl groups.

It is not apparent why the compound of the formula [I] gives a heat-sensitive recording material which is suited to high-speed recording and exhibits excellent resistances to plasticizer and diazo developer. However, these effects are presumed to be attributable to the fact that the compound having such a structure has a relatively low solubility in plasticizer and petroleums contained in diazo developer.

The present hydroxydiphenyl sulfone derivative of the formula [I] having excellent properties as stated above, can be prepared for example by the reaction of p-phenolsulfonyl halide [II] and a benzene derivative [III] as shown below. The derivative of the formula [I] can also be prepared by the reaction of phenol compound [IV] and an aromatic sulfonyl halide derivative [V].

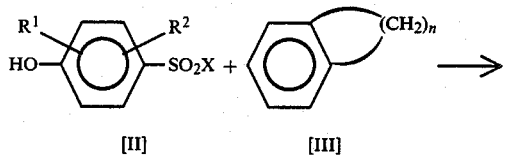

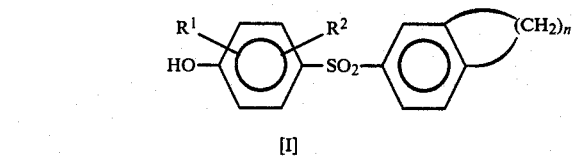

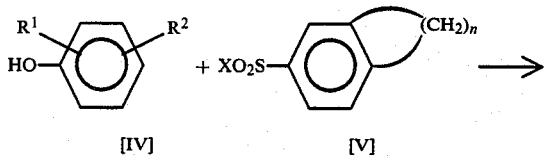

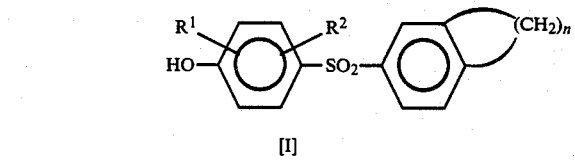

wherein X is halogen and $R^1$, $R^2$ and n are as defined above.

These condensation reactions are conducted at a temperature preferably of 5° to 150° C. in the presence of a condensing agent. Examples of useful condensing agents are anhydrous tin chloride, zinc chloride, anhydrous aluminum chloride, phosphorus trichloride, phosphorus tribromide, phosphorus pentachloride, boron trifluoride and like Friedal-Crafts catalysts, and these compounds are usable singly or in a mixture thereof. Solvents can be used such as carbon disulfide, monochlorobenzene, dichlorobenzene, dichloroethane, tetrachloroethane, nitrobenzene, nitromethane, nitroethane, etc.

Further, the present derivative can be prepared by heating a mixture of the compound represented by the formula [VI] and an aqueous solution of sodium hydroxide or potassium hydroxide preferably at 200° to 250° C.,

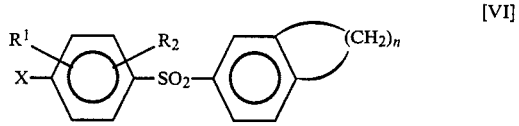

[VI]

wherein $R^1$, $R^2$, X and n are as defined above.

The present derivative can also be obtained by reacting the compound represented by the formula [VII] with a dealkylating agent such as aluminum chloride, aluminum bromide, boron tribromide, hydrogen bromide, hydrogen iodide, trimethylsilyl iodide, pyridinium hydrochloride, lithium iodide, etc.

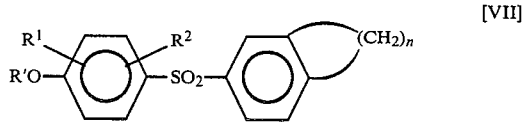

[VII]

wherein R' is lower alkyl and $R^1$, $R^2$ and n are as defined above.

Examples of the present compounds of the formula [I] thus obtained are as follows.

3',4'-trimethylene-4-hydroxydiphenyl sulfone
3',4'-trimethylene-2-methyl-4-hydroxydiphenyl sulfone
3',4'-trimethylene-3-methyl-4-hydroxydiphenyl sulfone
3',4'-trimethylene-2-methoxy-4-hydroxydiphenyl sulfone
3',4'-trimethylene-2-chloro-4-hydroxydiphenyl sulfone
3',4'-trimethylene-2,3-dimethyl-4-hydroxydiphenyl sulfone
3',4'-trimethylene-2,6-dimethyl-4-hydroxydiphenyl sulfone
3',4'-trimethylene-2,4-dihydroxydiphenyl sulfone
3',4'-trimethylene-3-methoxy-4-hydroxydiphenyl sulfone
3',4'-trimethylene-3-chloro-4-hydroxydiphenyl sulfone
3',4'-trimethylene-3,4-dihydroxydiphenyl sulfone
3',4'-trimethylene-3-chloro-5-methyl-4-hydroxydiphenyl sulfone
3',4'-trimethylene-2,5-dichloro-4-hydroxydiphenyl sulfone
3',4'-trimethylene-3,5-dichloro-4-hydroxydiphenyl sulfone
3',4'-trimethylene-3,5-dibromo-4-hydroxydiphenyl sulfone
3',4'-tetramethylene-4-hydroxydiphenyl sulfone
3',4'-tetramethylene-2-methyl-4-hydroxydiphenyl sulfone
3',4'-tetramethylene-3-methyl-4-hydroxydiphenyl sulfone
3',4'-tetramethylene-2-methoxy-4-hydroxydiphenyl sulfone
3',4'-tetramethylene-2-chloro-4-hydroxydiphenyl sulfone
3',4'-tetramethylene-2,3-dimethyl-4-hydroxydiphenyl sulfone
3',4'-tetramethylene-2,6-dimethyl-4-hydroxydiphenyl sulfone
3',4'-tetramethylene-2,4-dihydroxydiphenyl sulfone
3',4'-tetramethylene-3-methoxy-4-hydroxydiphenyl sulfone
3',4'-tetramethylene-3-chloro-4-hydroxydiphenyl sulfone
3',4'-tetramethylene-3,4-dihydroxydiphenyl sulfone
3',4'-tetramethylene-3-chloro-5-methyl-4-hydroxydiphenyl sulfone
3',4'-tetramethylene-2,5-dichloro-4-hydroxydiphenyl sulfone
3',4'-tetramethylene-3,5-dichloro-4-hydroxydiphenyl sulfone
3',4'-tetramethylene-3,5 -dibromo-4-hydroxydiphenyl sulfone As stated above, these hydroxydiphenyl sulfone derivatives exhibit excellent properties when used as a color acceptor of a heat-sensitive recording material. Applications of the derivative to the heat-sensitive recording material are shown below in detail.

In a heat-sensitive recording material incorporating a colorless or pale-colored basic dye and a color acceptor which is reactive with the dye to form a color when contacted therewith, the recording material of the present invention is characterized in that the color acceptor comprises at least one compound represented by the formula [I].

Various known colorless or pale-colored basic dyes are used in the recording layer of the present heat-sensitive recording material. Examples of useful dyes are:

Triarylmethane-based dyes, e.g., 3,3-bis(p-dimethylaminophenyl)-6-dimethylaminophthalide, 3,3-bis(p-dimethylaminophenyl)phthalide, 3-(p-dimethylaminophenyl)-3-(1,2-dimethylindole-3-yl)phthalide, 3-(p-dimethylaminophenyl)-3-(2-methylindole-3-yl)phthalide, 3,3-bis(1,2-dimethylindole-3-yl)-5-dimethylaminophthalide, 3,3-bis(1,2-dimethylindole-3-yl)-6-dimethylaminophthalide, 3,3-bis(9-ethylcarbazole-3-yl)-6-dimethylaminophthalide, 3,3-bis(2-phenylindole-3-yl)-6-dimethylaminophthalide, 3-p-dimethylaminophenyl-3-(1-methylpyrrole-3-yl)-6-dimethylaminophthalide, etc.

Diphenylmethane-based dyes, e.g., 4,4'-bis-dimethylaminobenzhydryl benzyl ether, N-halophenyl-leucoauramine, N-2,4,5-trichlorophenyl-leucoauramine, etc.

Thiazine-based dyes, e.g., benzoyl-leucomethyleneblue, p-nitrobenzoyl-leucomethyleneblue, etc.

Spiro-based dyes, e.g., 3-methyl-spiro-dinaphthopyran, 3-ethyl-spiro-dinaphthopyran, 3-phenyl-spiro-dinaphthopyran, 3-benzyl-spiro-dinaphthopyran, 3-methyl-naphtho-(6'-methoxybenzo)spiropyran, 3-propyl-spirodibenzopyran, etc.

Lactam-based dyes, e.g., rhodamine-B-anilinolactam, rhodamine-(p-nitroanilino)lactam, rhodamine-(o-chloroanilino)lactam, etc.

Fluoran-based dyes, e.g., 3-dimethylamino-7-methoxyfluoran, 3-diethylamino-6-methoxyfluoran, 3-diethylamino-7-methoxyfluoran, 3-diethylamino-7-chlorofluoran, 3-diethylamino-6-methyl-7-chlorofluoran, 3-diethylamino-6,7-dimethylfluoran, 3-(N-ethyl-p- toluidino)-7-methylfluoran, 3-diethylamino-7-(N-acetyl-N-methylamino)fluoran, 3-diethylamino-7-N-methylaminofluoran, 3-diethylamino-7-dibenzylaminofluoran, 3-diethylamino-7-(N-methyl-N-benzylamino)fluoran, 3-diethylamino-7-(N-chloroethyl-N-methylamino)fluoran, 3-diethylamino-7-N-diethylaminofluoran, 3-(N-ethyl-p-toluidino)-6-methyl-7-phenylaminofluoran, 3-(N-ethyl-p-toluidino)-6-methyl-7-(p-toluidino)fluoran, 3-diethylamino-6-methyl-7-phenylaminofluoran, 3-dibutylamino-6-methyl-7-phenylaminofluoran, 3-(N-ethyl-N-cyclopentylamino)-6-methyl-7-phenylaminofluoran, 3-(N-cyclohexyl-N-methylamino)-6-methyl-7-phenylaminofluoran, 3-pyrrolidino-6-methyl-7-phenylaminofluoran, 3-piperidino-6-methyl-7-phenylaminofluoran, 3-diethylamino-6-methyl-7-xylidinofluoran, 3-(N-methyl-N-isoamylamino)-6-methyl-7-phenylaminofluoran, 3-(N-ethyl-N-isoamylamino)-6-methyl-7-phenylaminofluoran, 3-(N-methyl-N-n-hexylamino)-6-methyl-7-phenylaminofluoran, 3-(N-ethyl-N-n-hexylamino)-6-methyl-7-phenylaminofluoran, 3-(N-ethyl-N-tetrahydrofurfurylamino)-6-methyl-7-phenylaminofluoran, 3-diethylamino-7-(2-carbomethoxy-phenylamino)fluoran, 3-diethylamino-7-(o-chlorophenylamino)fluoran, 3-dibutylamino-7-(o-chlorophenylamino)fluoran, 3-dibutylamino-7-(o-fluorophenylamino)fluoran, etc. The basic dyes of the invention are not limited thereto. Further, these dyes can be used singly or in mixture of at least two of them.

With the heat-sensitive recording materials of the invention, the proportions of the color acceptor and the basic dye are not particularly limited. The former is used in an amount of preferably 100 to 700 parts by weight, more preferably 150 to 400 parts by weight per 100 parts by weight of the latter.

For preparing a coating composition comprising the foregoing components, the basic dye and the color acceptor are dispersed, together or individually, into water serving as a dispersion medium, using stirring and pulverizing means such as a ball mill, attritor or sand mill. Usually the coating composition has incorporated therein a binder in an amount of 10 to 40% by weight, preferably 15 to 30% by weight, based on the total solids content of the composition. Examples of useful binders are starches, hydroxyethyl cellulose, methyl cellulose, carboxymethyl cellulose, gelatin, casein, gum arabic, polyvinyl alcohol, styrene-maleic anhydride copolymer salt, styrene-acrylic acid copolymer salt, styrene-butadiene copolymer emulsion, etc. Various other auxiliary agents can be further added to the coating composition. Examples of useful agents are dispersants such as sodium dioctylsulfosuccinate, sodium dodecylbenzene-sulfonate, sodium lauryl sulfate, fatty acid metal salts, etc., ultraviolet absorbers such as triazole compounds, defoaming agents, fluorescent dyes, coloring dyes, etc.

Further, to the composition may be added, in order to prevent sticking upon contact of the heat-sensitive recording paper with a recording device or thermal head, a dispersion or emulsion of stearic acid, polyethylene, carnauba wax, paraffin wax, zinc stearate, calcium stearate, ester wax or the like.

Further, to the composition may be added in an amount which does not cause adverse effect, aliphatic fatty acid amide such as stearic acid amide, stearic acid methylenebisamide, oleic acid amide, palmitic acid amide, coconut fatty acid amide, etc; hindered phenols such as 2,2'-methylene-bis(4-methyl-6-tert-butylphenol), 1,1,3-tris(2-methyl-4-hydroxy-5-tert-butylphenyl)butane, etc; ethers such as 1,2-bis(phenoxy)ethane, 1,2-bis(4-methylphenoxy)ethane, 1,2-bis(3-methylphenoxy)ethane, 2-naphthol benzyl ether, etc; esters such as dibenzyl terephthalate, 1-hydroxy-2-naphthoic acid phenyl ester, etc; and various known heat-fusible substances.

In addition, to the composition may be added in order to prevent the adhesion of tailings to the thermal head, inorganic pigment such as kaolin, clay, talc, calcium carbonate, calcined clay, titanium oxide, kieselguhr, finely divided anhydrous silica, activated clay, etc.

The present heat-sensitive recording material is characterized in that at least one of the above specific hydroxydiphenyl sulfone derivatives is used as a color acceptor. It is possible, however, to use conjointly other color acceptors such as 4,4'-isopropylidenediphenol, 4,4'-cyclohexylidenediphenol, benzyl 4-hydroxybenzoate, dimethyl 4-hydroxyphthalate, etc.

As a substrate (support) to be coated, may be used a paper, plastic film, synthetic fiber sheet or the like, but a paper is most preferably used from a viewpoint of cost, coating applicability, etc. The amount of coating composition forming the recording layer to be applied to the support, which is not limited particularly, is usually about 2 to 12 g/m$^2$, preferably about 3 to 10 g/m$^2$, based on dry weight. Further, it is possible to form an over-coat layer on the recording layer to protect the layer. Various other known techniques in the field of heat-sensitive recording material can be applied. For example, it is possible to form a protect layer on the rear surface of the support, to form a primary coating layer on the support.

The heat-sensitive recording materials thus obtained suit to high-speed recording, give colorfast record images and are free from the fogging in the background and from extraneous deposits on the thermal head (piling).

The invention will be described below in more detail with reference to Examples by no means limited to, in which parts and percentages are all by weight, unless otherwise specified.

EXAMPLE 1

To 100 ml of methanesulfonic acid was added 40 g of phosphorus pentoxide at room temperature with stirring. Thereto were added 25 ml of indan and 45 g of sodium p-anisolesulfonate. The mixture was stirred for 6 hours and then poured into a 1-liter quantity of cooled water to obtain precipitates. The precipitate was filtered, washed with water and dried at a reduced pressure to obtain 3',4'-trimethylene-4-methoxydiphenyl sulfone.

The compound was dissolved in 300 ml of benzene and thereto was added 60 g of anhydrous aluminum chloride. The mixture was refluxed for 1 hour. The product was, after cooled, poured into 1 liter of ice water to obtain precipitates. The precipitate was filtered, washed with water and recrystallized from benzene to give 49 g of 3',4'-trimethylene-4-hydroxydiphenyl sulfone (m.p. 174° to 176° C.).

EXAMPLE 2

3',4'-Trimethylene-2,6-dimethyl-4-hydroxydiphenyl sulfone (m.p. 183° to 187° C.) was obtained in a yield of 53 g in the same manner as in Example 1 except that 48 g of sodium 2,6-dimethyl-4-methoxybenzenesulfonate was used in place of 45 g of sodium p-anisolesulfonate.

EXAMPLE 3

3',4'-Tetramethylene-4-hydroxydiphenyl sulfone (m.p. 132° to 133° C.) was prepared in a yield of 50 g in the same manner as in Example 1 except that 27 g of tetralin was used in place of 25 ml of indan.

EXAMPLE 4

3',4'-Tetramethylene-2-methyl-4-hydroxydiphenyl sulfone (m.p. 144° to 145° C.) was prepared in a yield of 56 g in the same manner as in Example 1 except that 27 g of tetralin and 47 g of sodium 4-methoxy-2-methylbenzenesulfonate were used respectively in place of 25 ml of indan and 45 g of sodium p-anisolesulfonate.

EXAMPLE 5

3',4'-Tetramethylene-3-methyl-4-hydroxydiphenyl sulfone (m.p. 169° to 170° C.) was prepared in a yield of 54 g in the same manner as in Example 1 except that 27 g of tetralin and 47 g of sodium 4-methoxy-3-methylbenzenesulfonate were used respectively in place of 25 ml of indan and 45 g of sodium p-anisolesulfonate.

EXAMPLE 6

3',4'-Tetramethylene-3,4-dihydroxydiphenyl sulfone (m.p. 155° to 157° C.) was prepared in a yield of 59 g in the same manner as in Example 1 except that 27 g of tetralin and 50 g of sodium veratrol-4-sulfonate were used respectively in place of 25 ml of indan and 45 g of sodium p-anisolesulfonate, and 90 g of anhydrous aluminum chloride was used in the demethylation reaction in place of 60 g thereof.

EXAMPLE 7

3',4'-tetramethylene-3-chloro-4-hydroxydiphenyl sulfone (m.p. 151° to 154° C.) was prepared in a yield of 45 g in the same manner as in Example 1 except that 27 g of tetralin and 52 g of sodium 3-chloro-4-methoxybenzenesulfonate were used respectively in place of 25 ml of indan and 45 g of sodium p-anisolesulfonate.

EXAMPLE 8

Into 500 ml of 1,2-dichloroethane were dissolved 45 g of 4-hydroxy-3-methoxybenzenesulfonyl chloride and 50 g of tetralin. The solution was stirred at room temperature and 55 g of anhydrous aluminum chloride was gradually added thereto. The mixture was stirred at room temperature for 6 hours and then allowed to place over night. The reaction mixture was poured into a mixture of ice and diluted hydrochloric acid. The organic layer was throughly washed with water and dried with anhydrous sodium sulfate. The solvent was distilled off at a reduced pressure and the residue was recrystallized from toluene to give 51 g of 3',4'-tetramethylene-3-methoxy-4-hydroxydiphenyl sulfone (m.p. 128° to 132° C.).

EXAMPLE 9

(1) Composition (A)

3-(N-cyclohexyl-N-methylamino)-6-methyl-7-phenylaminofluoran (10 parts), 20 parts of stearic acid amide, 15 parts of 5% aqueous solution of methyl cellulose and 120 parts of water were pulverized by a sand mill to prepare Composition (A) having an average particle size of 3 μm.

(2) Composition (B)

3',4'-Trimethylene-4-hydroxydiphenyl sulfone (30 parts), 30 parts of 5% aqueous solution of methyl cellulose and 70 parts of water were pulverized by a sand mill to obtain Composition (B) having an average particle size of 3 μm.

(3) Preparation of a recording layer

A 165-part quantity of Composition (A), 130 parts of Composition (B), 30 parts of finely divided anhydrous silica (oil absorption: 180 ml/100 g), 150 parts of 20% aqueous solution of oxidized starch and 55 parts of water were mixed with stirring to prepare a coating composition. The coating composition was applied to a paper substrate weighing 50 g/m$^2$ in an amount of 7.5 g/m$^2$ by dry weight to prepare a heat-sensitive recording paper.

EXAMPLE 10

A heat-sensitive recording paper was prepared in the same manner as in Example 9 except that 3',4'-trimethylene-2,6-dimethyl-4-hydroxydiphenyl sulfone was used in place of 3',4'-trimethylene-4-hydroxydiphenyl sulfone in the preparation of Composition (B).

EXAMPLE 11

A heat-sensitive recording paper was prepared in the same manner as in Example 9 except that 3',4'-tetramethylene-4-hydroxydiphenyl sulfone was used in place of 3',4'-trimethylene-4-hydroxydiphenyl sulfone in the preparation of Composition (B).

EXAMPLE 12

A heat-sensitive recording paper was prepared in the same manner as in Example 9 except that 3',4'-tetramethylene-2-methyl-4-hydroxydiphenyl sulfone was used in place of 3',4'-trimethylene-4-hydroxydiphenyl sulfone in the preparation of Composition (B).

EXAMPLE 13

A heat-sensitive recording paper was prepared in the same manner as in Example 9 except that 3',4'-tetramethylene-3,4-dihydroxydiphenyl sulfone was used in place of 3',4'-trimethylene-4-hydroxydiphenyl sulfone in the preparation of Composition (B).

EXAMPLE 14

A heat-sensitive recording paper was prepared in the same manner as in Example 9 except that 3',4'-tetramethylene-3-chloro-4-hydroxydiphenyl sulfone was used in place of 3',4'-trimethylene-4-hydroxydiphenyl sulfone in the preparation of Composition (B).

EXAMPLE 15

A heat-sensitive recording paper was prepared in the same manner as in Example 9 except that 3',4'-tetramethylene-3-methyl-4-hydroxydiphenyl sulfone was used in place of 3',4'-trimethylene-4-hydroxydiphenyl sulfone in the preparation of Composition (B).

EXAMPLE 16

A heat-sensitive recording paper was prepared in the same manner as in Example 9 except that 3',4'-tetramethylene-3-methoxy-4-hydroxydiphenyl sulfone was used in place of 3',4'-trimethylene-4-hydroxydiphenyl sulfone in the preparation of Composition (B).

COMPARISON EXAMPLE 1

A heat-sensitive recording paper was prepared in the same manner as in Example 9 except that 4,4'-isopropylidenediphenol was used in place of 3',4'- trimethylene-4-hydroxydiphenyl sulfone in the preparation of Composition (B).

COMPARISON EXAMPLE 2

A heat-sensitive recording paper was prepared in the same manner as in Example 9 except that 4-hydroxy-4'-methyldiphenyl sulfone was used in place of 3',4'-trimethylene-4-hydroxydiphenyl sulfone in the preparation of Composition (B).

The ten kinds of heat-sensitive recording papers thus prepared were fed to a heat-sensitive facsimile system (Hitachi HIFAX-700 Model, a product of Hitachi Ltd.) for recording and checked for color density ($D_0$) by Macbeth densitometer (Model RD-100R, with an amber filter, a product of Macbeth Corp.). Table 1 shows the results.

Each of the heat-sensitive recording papers was superposed on a polyvinyl chloride film after recording, and checked for color density ($D_1$) after 1 hour by Macbeth densitometer. The results were given in Table 1.

Further, each of the heat-sensitive recording papers was checked for whiteness of the recording layer with use of a Hunter multipurpose reflectometer before recording. A paper impregnated with diazo developer (SD type, a product of Ricoh Co., Ltd.) was superposed on the heat-sensitive recording paper for 5 minutes and thereafter the whiteness of the recording layer was measured. Table 1 shows the results.

TABLE 1

|  | Color density ($D_0$) | Color density after plasticizer test ($D_1$) | Whiteness (%) | Whiteness after diazo developer test (%) |
| --- | --- | --- | --- | --- |
| Ex. 9 | 1.29 | 1.23 | 82.3 | 80.9 |
| Ex. 10 | 1.28 | 1.20 | 82.7 | 81.0 |
| Ex. 11 | 1.32 | 1.26 | 82.7 | 81.9 |
| Ex. 12 | 1.30 | 1.26 | 82.5 | 82.0 |
| Ex. 13 | 1.33 | 1.28 | 82.4 | 81.4 |
| Ex. 14 | 1.32 | 1.25 | 82.5 | 81.1 |
| Ex. 15 | 1.28 | 1.22 | 82.2 | 81.2 |
| Ex. 16 | 1.33 | 1.24 | 82.6 | 81.8 |
| Com. Ex. 1 | 0.83 | 0.23 | 80.6 | 51.7 |
| Com. Ex. 2 | 1.15 | 0.78 | 81.8 | 68.3 |

As apparent from Table 1, the present heat-sensitive recording paper suits to high-speed recording and has excellent resistances to plasticizer and diazo developer.

What is claimed is:

1. In a heat-sensitive recording material incorporating a colorless or pale-colored basic dye and a color acceptor which is reactive with the dye to form a color when contacted therewith, the recording material characterized in that the color acceptor comprises at least one hydroxydiphenyl sulfone derivative represented by the formula [I]

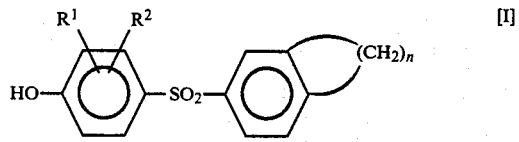

wherein $R^1$ and $R^2$ are each hydrogen, halogen, lower alkyl, lower alkoxy or hydroxyl and n is an integer of 3 or 4.

2. A heat-sensitive recording material as defined in claim 1 wherein the color acceptor represented by the formula [I] is used in an amount of 100 to 700 parts by weight per 100 parts by weight of the basic dye.

* * * * *